US012758671B2

(12) United States Patent
Turan

(10) Patent No.: US 12,758,671 B2
(45) Date of Patent: Oct. 13, 2026

(54) ODOR CONTROL SYSTEM FOR LANDFILLS AND ASSOCIATED METHODS

(71) Applicant: JPC HOLDINGS, LLC, Chicago, IL (US)

(72) Inventor: Nevzat Turan, Fort Worth, TX (US)

(73) Assignee: JPC HOLDINGS, LLC, Naperville, IL (US)

( * ) Notice: Subject to any disclaimer, the term of this patent is extended or adjusted under 35 U.S.C. 154(b) by 868 days.

(21) Appl. No.: 17/842,061

(22) Filed: Jun. 16, 2022

(65) Prior Publication Data

US 2022/0401611 A1 Dec. 22, 2022

Related U.S. Application Data

(60) Provisional application No. 63/211,146, filed on Jun. 16, 2021.

(51) Int. Cl.

*A61L 9/12* (2006.01)
*A61L 9/04* (2006.01)
*A61L 101/20* (2006.01)

(52) U.S. Cl.

CPC ............... *A61L 9/122* (2013.01); *A61L 9/042* (2013.01); *A61L 2101/20* (2020.08); *A61L 2209/134* (2013.01); *A61L 2209/21* (2013.01)

(58) Field of Classification Search

None

See application file for complete search history.

(56) References Cited

U.S. PATENT DOCUMENTS

| | | | | |
|---|---|---|---|---|
| 4,405,354 | A | 9/1983 | Thomas, II et al. | |
| 4,795,590 | A | 1/1989 | Kent et al. | |
| 4,816,220 | A | 3/1989 | Roychowdhury | |
| 4,992,206 | A | 2/1991 | Waldron | |
| 5,849,364 | A | 12/1998 | Nachtman et al. | |
| 5,865,143 | A * | 2/1999 | Moore, Jr. ................ | A61L 9/01 239/210 |

(Continued)

OTHER PUBLICATIONS

Cleanawater—QuikAir(R) V Concentrate. QuikAir(R) V Vapour Guard Odour Treatment Brochure, [online] [retrieved on Mar. 13, 2025] evidenciary reference. pp. 1-2. https://cleanawater.com.au/assets/Uploads/Brochures/Cleanawater-QuikAirA4-202305.pdf (Year: 2023).*

(Continued)

*Primary Examiner* — Jelitza M Perez

(74) *Attorney, Agent, or Firm* — ALLEN, DYER, DOPPELT + GILCHRIST, P.A.

(57) ABSTRACT

An odor control system for landfills includes a vapor device configured to generate an odor neutralizing chemical mixture, and at least one fan directed at a working face of a landfill. The at least one fan includes a fan housing having an inlet opening and a discharge opening connected by a passageway therethrough, a blade assembly positioned within the passageway of the fan housing and configured to rotate to generate an airflow from the discharge opening in a first direction, and a motor coupled to the blade assembly. The system includes at least one nozzle in fluid communication with the vapor device and proximate the discharge opening. The at least one nozzle is configured to disperse an odor neutralizing chemical vapor in the same first direction of the airflow from the discharge opening.

11 Claims, 6 Drawing Sheets

(56) References Cited

U.S. PATENT DOCUMENTS

| | | | | |
|---|---|---|---|---|
| 6,296,446 | B1 | 10/2001 | Ishijima et al. | |
| 6,595,037 | B2 | 7/2003 | McGinley | |
| 6,669,105 | B2 | 12/2003 | Bryan et al. | |
| 6,722,588 | B1 | 4/2004 | Elkas | |
| 6,743,421 | B2 | 6/2004 | Vasconcellos et al. | |
| 8,475,718 | B2 | 7/2013 | Sifers et al. | |
| 9,028,751 | B2 | 5/2015 | Page et al. | |
| 9,066,509 | B2 | 6/2015 | Victorio Da Costa | |
| 9,303,177 | B2 | 4/2016 | Donze et al. | |
| 10,208,770 | B2 | 2/2019 | Arai et al. | |
| 2013/0091757 | A1 | 4/2013 | Victorio Da Costa | |
| 2019/0038793 | A1* | 2/2019 | Byers | B01D 1/0082 |
| 2019/0143349 | A1* | 5/2019 | Lewis | B05B 7/0075 239/101 |
| 2020/0306403 | A1* | 10/2020 | Byers | A61L 9/05 |

OTHER PUBLICATIONS

Cleanawater—QuikAir(R) V Concentrate. QuikAir(R) V Vapour Guard Odor Treatment Brochure. [online] [retrieved on Aug. 26, 2025], evidenciary reference. pp. 1-2. https://cleanawater.com.au/assets/Uploads/Brochures/Cleanawater-QuikAirA4-202305.pdf (Year: 2023).*

Cleanawater—QuikAir(R)V Concentrate. QuikAir(R)V Vapour Guard Odor Treatment Brochure.[online] [retrieved on Dec. 9, 2025], evidentiary reference.pp. 1-2. https://cleanawater.com.au/assets/Uploads/Brochures/Cleanawater-QuikAirA4-202305.pdf (Year: 2023).*

* cited by examiner

ODOR CONTROL SYSTEM FOR LANDFILLS AND ASSOCIATED METHODS

RELATED APPLICATIONS

This application claims priority to U.S. Provisional Application Ser. No. 63/211,146 filed on Jun. 16, 2021 the contents of which are herein incorporated by reference in their entirety.

FIELD OF THE INVENTION

The present invention relates to the field of odor control, and more particularly to an odor control system for landfills and associated methods.

BACKGROUND

Landfills are used to concentrate waste in a particular geographic location. While landfills reduce the amount of waste in the environment, the waste stream for landfills has concentrated putrid materials that emit offensive odors. These odors are a nuisance for anyone living near a landfill. As a result, a need has developed to mitigate the offensive odors from landfills.

While there have been improvements to address the offensive odors, the existing systems are expensive and often difficult to operate and maintain. Accordingly, there is a need for an odor mitigation system that is effective for neutralizing (or deodorizing) odorous chemicals and easy to operate and maintain.

SUMMARY

In a particular illustrative embodiment, an odor control system for landfills is disclosed. The odor control system includes a vapor device configured to generate an odor neutralizing chemical mixture, and at least one fan directed at a working face of a landfill. The at least one fan includes a fan housing having an inlet opening and a discharge opening connected by a passageway therethrough, a blade assembly positioned within the passageway of the fan housing and configured to rotate to generate an airflow from the discharge opening in a first direction, and a motor coupled to the blade assembly and configured to drive the blade assembly. In addition, the system includes at least one nozzle in fluid communication with the vapor device and proximate the discharge opening. The at least one nozzle is configured to disperse an odor neutralizing chemical vapor in the same first direction of the airflow from the discharge opening.

In a particular aspect, the odor neutralizing chemical vapor comprises at least one chemical from an amino hydroxyl group, and the fan housing comprises a cylindrical shape. The blade assembly may include a plurality of blades extending outward from a central hub and the motor may be positioned within the passageway of the fan housing. The system may also include a manifold coupled to the at least one nozzle, and the at least one nozzle may be positioned downstream of the discharge opening.

The odor control system may include an odor neutralizing chemical supply in fluid communication with the vapor device, where the at least one nozzle is configured to generate the vapor from the odor neutralizing chemical supply. The odor neutralizing chemical vapor comprises an odor neutralizing chemical that is entrained into the airflow.

The odor control system may also include a plurality of contiguous pipes disposed parallel to a ground surface and along a perimeter of a landfill, with each of the pipes comprising a plurality of nozzles. In addition, the system may have a plurality of vertical support columns carrying the plurality of pipes above the ground surface, and a dry vapor in fluid communication with the plurality of pipes and configured to be dispersed through the plurality of nozzles. A dry vapor device may be in fluid communication with the odor neutralizing chemical supply and configured to generate the dry vapor.

Another aspect relates to an odor control apparatus for a landfill. The apparatus includes a mobile platform configured to be moved to temporary locations proximate a working face of the landfill, and an odor control system carried by the mobile platform.

Another aspect relates to a method of operating an odor control system having at least one fan comprising a fan housing having an inlet opening and a discharge opening connected by a passageway therethrough, a blade assembly positioned within the passageway of the fan housing, and at least one nozzle proximate the discharge opening, and a dry vapor device configured to generate an odor neutralizing chemical vapor. The method includes rotating the blade assembly to generate an airflow from the discharge opening in a first direction, generating the odor neutralizing chemical vapor, and dispersing the odor neutralizing chemical vapor from the at least one nozzle at the discharge opening. The odor neutralizing chemical vapor includes an odor neutralizing chemical that is entrained into the airflow.

DETAILED DESCRIPTION

The present description is made with reference to the accompanying drawings, in which exemplary embodiments are shown. However, many different embodiments may be used, and thus the description should not be construed as limited to the particular embodiments set forth herein.

Rather, these embodiments are provided so that this disclosure will be thorough and complete. Like numbers refer to like elements throughout.

An odor control system for landfills of the present invention may be configured in two phases. The first phase ("Phase I") is directed to using fans to control odor from a landfill working face. In particular, the system may include using a hydrated vapor, which is a combination of water and chemicals, or a vaporized nonaqueous chemical, in a mobile system with fans that is configured to be moved and placed proximate to the working face of the landfill in order to neutralize the odor molecules before they leave the working (or active) face. The fans are strategically placed to maximize the likelihood of binding neutralizing chemical with odorous chemicals.

The second phase ("Phase II") is directed to controlling odor at the perimeter around a landfill using dry vapor. For example, after Phase I is effectively deployed using a hydrated vapor or a vaporized nonaqueous chemical, a dry vapor may be dispersed in Phase II. The dry vapor is generated from odor neutralizing chemicals using dry vapor devices. The dry vapor is dispersed using contiguous piping positioned along designated areas at the perimeter of the landfill.

With respect to Phase I, multiple fans may be deployed to provide the vapor at the working face of the landfill. The hydrated vapor is directed by the fans to effectively intercept air moving out of the working face in both vertical and horizontal directions. The small vaporized particles increase the probability to intercepting odorous chemicals by traveling long distances both vertically and horizontally from the fans, and by the maximum possible number of particles per unit volume of ambient air. In addition, the hydrated vapor (or vaporized noaqueous chemical) minimizes daily water consumption and maximizes air volume that carriers water particles. The fans are also easy to relocate, operate and to maintain. In a particular aspect, the operation of the system may not be affected by fuel and water outages since the fans and associated equipment may be located on self-contained mobile units (e.g., trailers).

The odor neutralizing chemicals used with the system may include chemicals from the amino hydroxyl group. The odor control chemicals can be delivered through aqueous or nonaqueous vapor that have been tested and verified to be configured to neutralize common working face odors from landfills. Also, consideration of the health and safety aspects of the odor control chemical are considered along with associated costs of the chemicals.

Figure 1:
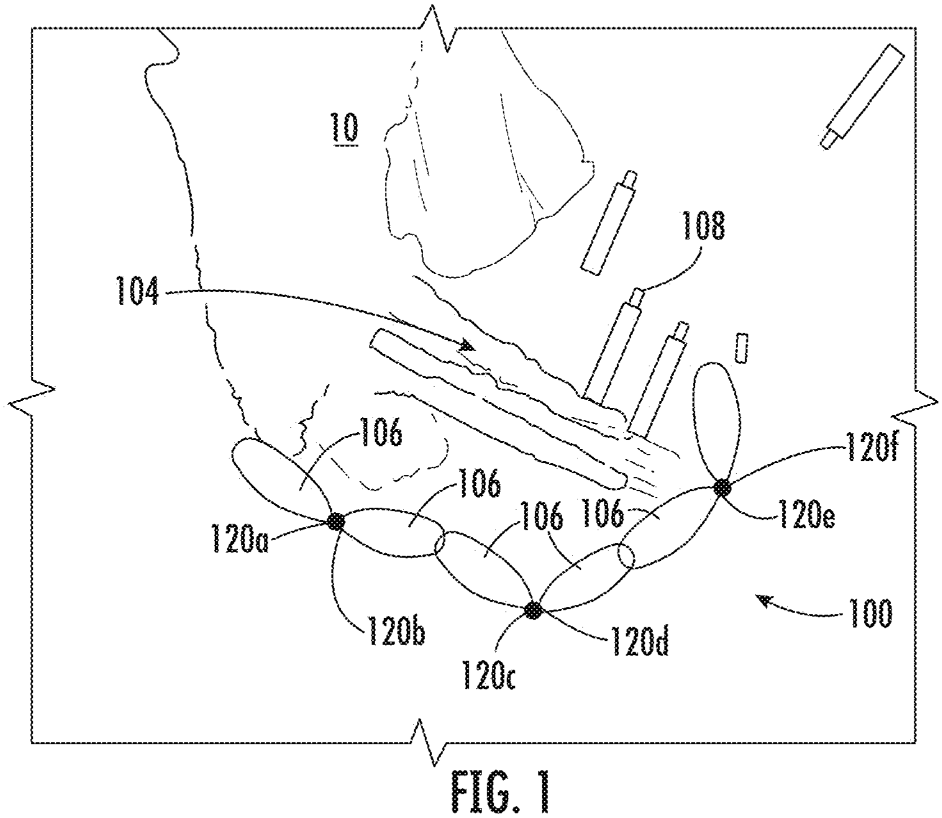
FIG. 1 is a schematic of an odor control system in which various aspects of the disclosure may be implemented.

Referring now to FIG. 1, a plan view of the odor control system for landfills is generally designated 100. A plurality of fans 102*a*, 102*b*, 102*c* are shown distributed adjacent to the working face 104 of a landfill 10. The fans 102*a*, 102*b*, 102*c* are configured to work together to produce an odor control barrier 106 that forms a suspended volume of odor neutralizing chemical vapor around the working face 104. The fans 102*a*, 102*b*, 102*c* are adjusted to direct the airflow midway towards the working face 104 and towards adjacent fans so that the airflow from each of the adjacent fans overlaps as shown in FIG. 1.

Figure 2:
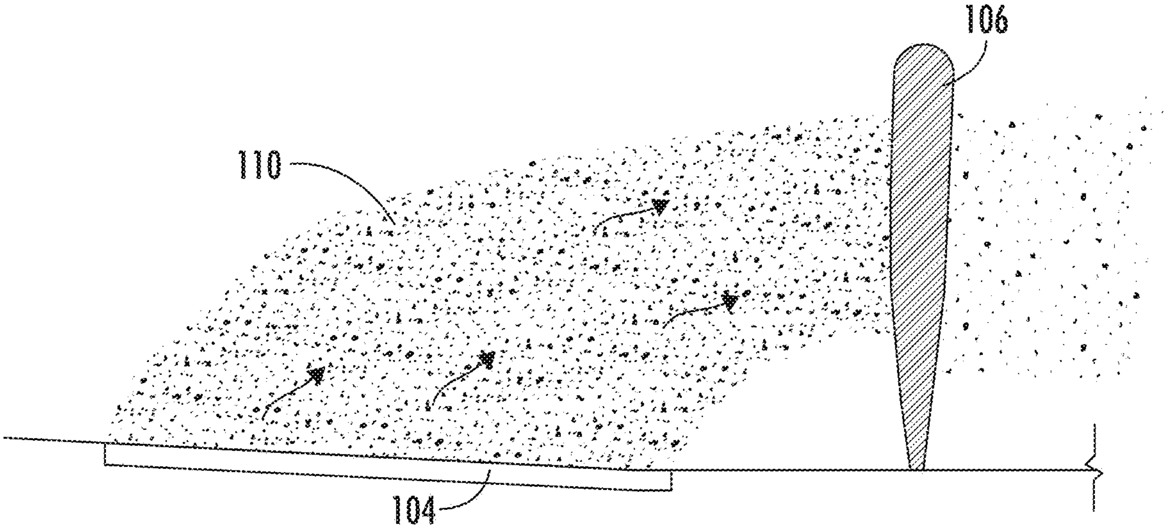
FIG. 2 is a schematic of operation of the odor control system of FIG. 1.

Accordingly, as trucks 108 empty trash onto the working face 104, the odorous chemicals 110 are mostly neutralized and contained within the odor control barrier 106 as shown in FIG. 2 without escaping into the surrounding areas causing a nuisance.

Figure 3:
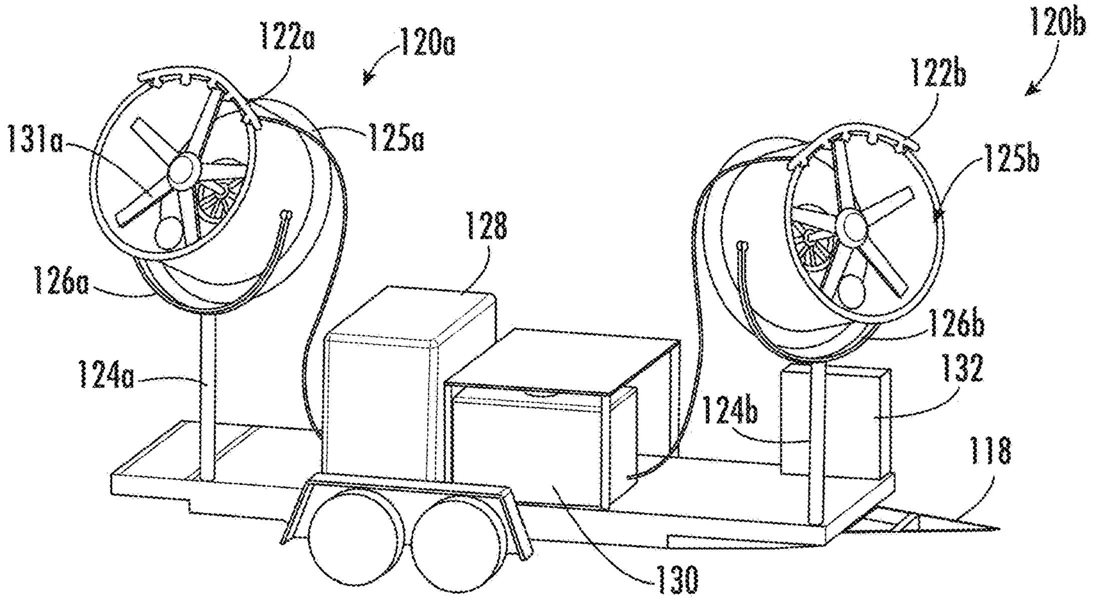
FIG. 3 is a front perspective view of a first embodiment of the odor control system using hydrated vapor.
Figure 4:
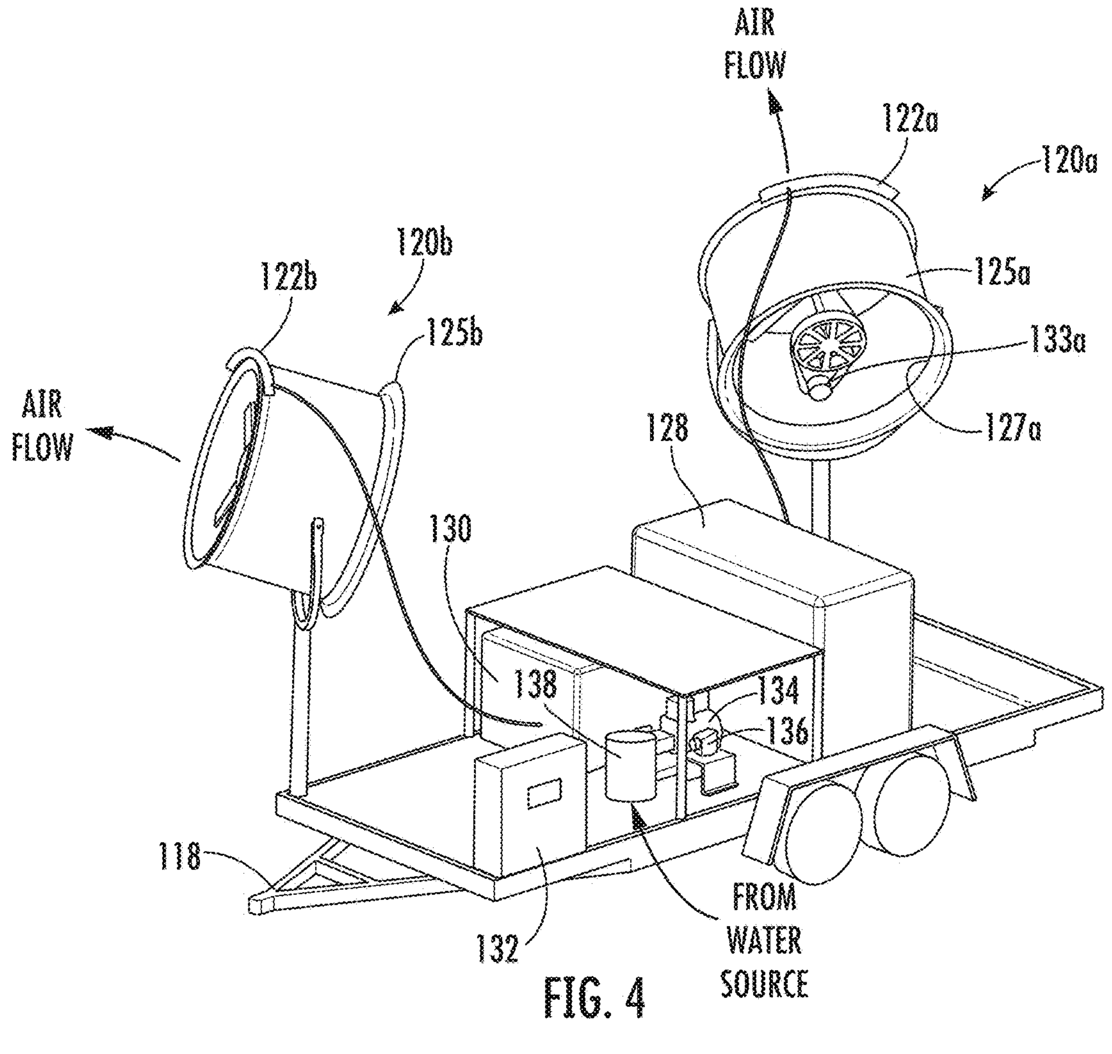
FIG. 4 is a rear perspective view of the odor control system of FIG. 3.

Referring now to FIGS. 3 and 4, the fans 120*a*, 120*b* are mounted to a trailer 118. The trailer 118 provides a mobile platform to mount one or more fans 120*a*, 120*b*. The fans 120*a*, 120*b* may each provide about 42,400 cfm of air flow in a particular aspect and have an effective reach of about 200 feet. The fans 120*a*, 120*b* are configured to prevent and reduce downward flow of moisture by the fans. The fans 120*a*, 120*b* each include a fan housing having an inlet opening and a discharge opening connected by a passageway therethrough and the fans are configured to be adjusted on location in order to change a discharge direction. For example, the fans 120*a*, 120*b* may be mounted atop respective posts 124*a*, 124*b* and can be rotated for horizontal adjustment. A mounting cradle 126*a*, 126*b* for the fans 120*a*, 120*b* is configured to swivel for vertical adjustment.

Each of the fans 102*a*, 102*b*, may be equipped with a respective manifold 122*a*, 122*b*. In a particular embodiment, each fan may have a plurality of nozzles coupled to the respective manifold. The nozzles are configured to efficiently provide a water and chemical mixture that may be as small as 20 gph per fan, for example. A hydrated vapor device 130 is in fluid communication with the water and odor neutralizing chemicals to generate an odor neutralizing chemical mixture that is pumped to the nozzles. The vapor dispersed by the nozzles may be approximately 25 microns in order to ensure the entire airflow is moisturized. A generator 128 may also be mounted to the trailer 118 to power the fans 120*a*, 120*b*, a water pump 134, and a chemical pump 136. A control panel 132 is used to control the pumps to adjust the water and chemical mixture and flow rates of pumps. A water filter 138 may be upstream from the water pump 134 and connected to a water source such as a water tank.

Figure 5A:
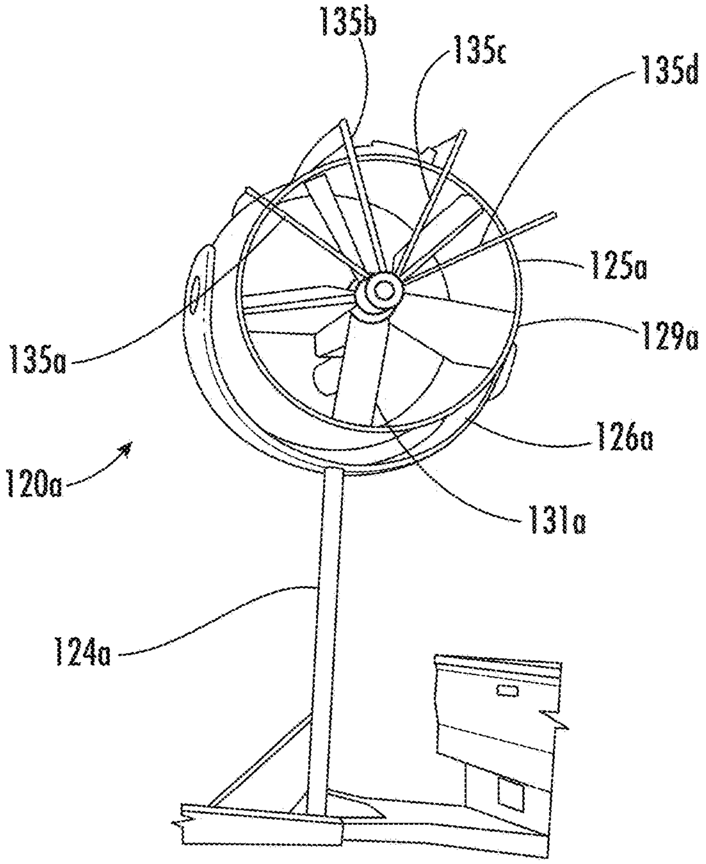
FIG. 5A is a detail view of a fan of the first embodiment of the odor control system.
Figure 5B:
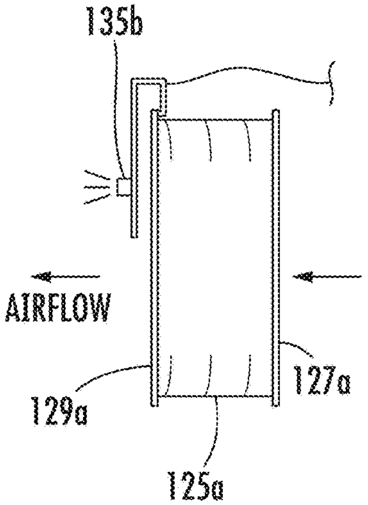
FIG. 5B is a detail view of the fan housing and configuration of a nozzle of the first embodiment of the odor control system.

Referring now to FIG. 5A, detail view of the fan 120*a* is depicted. FIG. 5B depicts a schematic of the fan housing 125*a* and the configuration of the nozzle 135*b* with respect to the discharge opening 129*a*. Each of the fans of the system 100 have similar construction. For example, the fan 120*a* includes a fan housing 125*a* having an inlet opening 127*a* and a discharge opening 129*a* connected by a passageway therethrough. A blade assembly 131*a* is positioned within the passageway of the fan housing 125*a* and is configured to rotate to generate an airflow from the discharge opening 129*a* in a first direction. A motor 133*a* is coupled to the blade assembly 131*a* and is configured to drive the blade assembly 131*a*. In addition, a plurality of nozzles 135*a*, 135*b*, 135*c*, 135*d* are in fluid communication with the hydrated vapor device 130 and proximate the discharge opening 129*a* where each nozzle has an aperture aligned with the passageway and may be facing in the first direction. The nozzles 135*a*, 135*b*, 135*c*, 135*d* are configured to disperse the odor neutralizing chemical vapor in the same first direction of the airflow from the discharge opening 129*a*.

Figure 6:
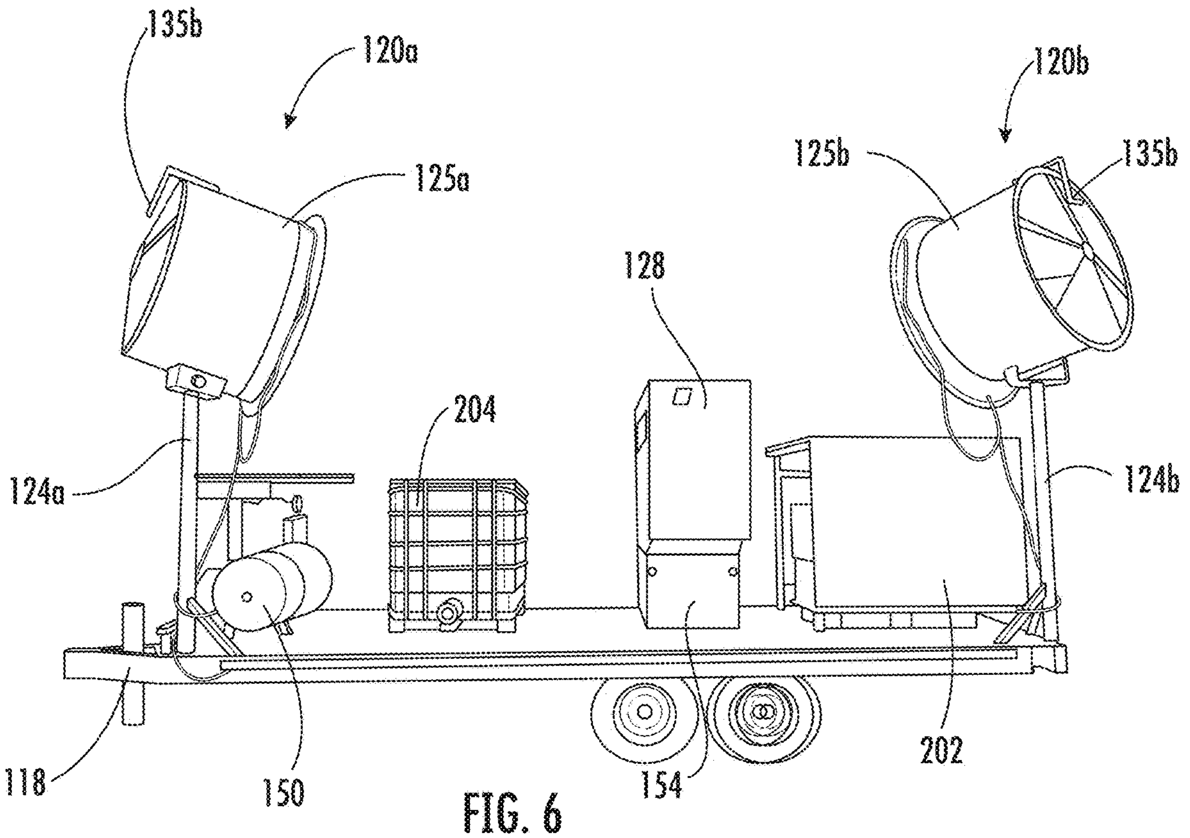
FIG. 6 is an elevational view of a second embodiment of the odor control system using dry vapor.
Figure 7:
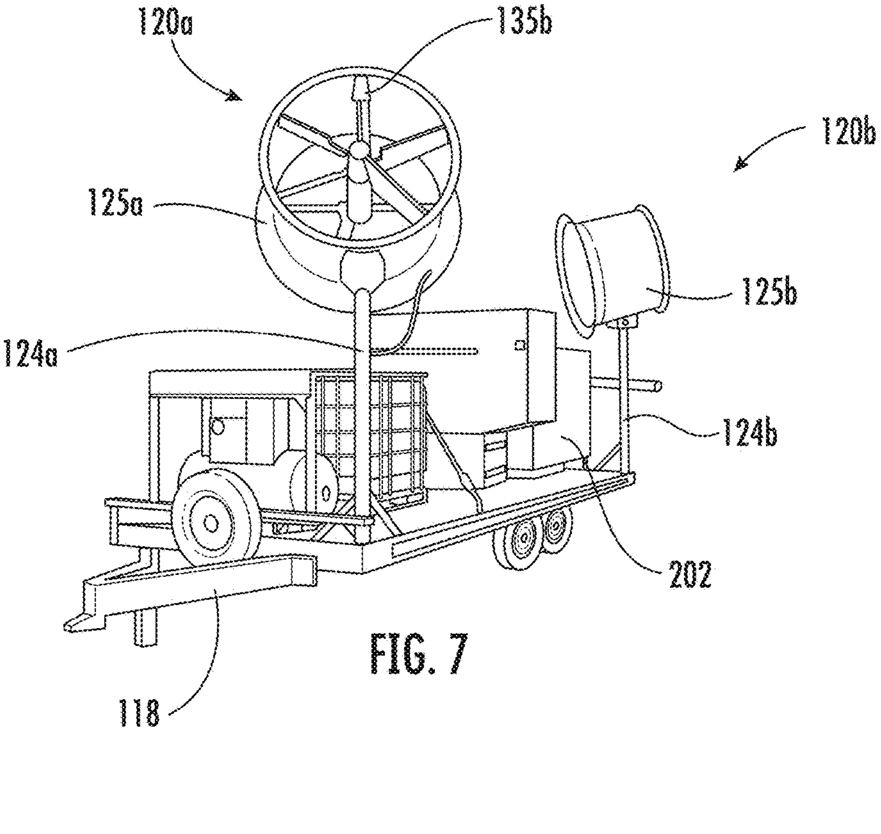
FIG. 7 is a perspective view of the odor control system of FIG. 6.
Figure 8:
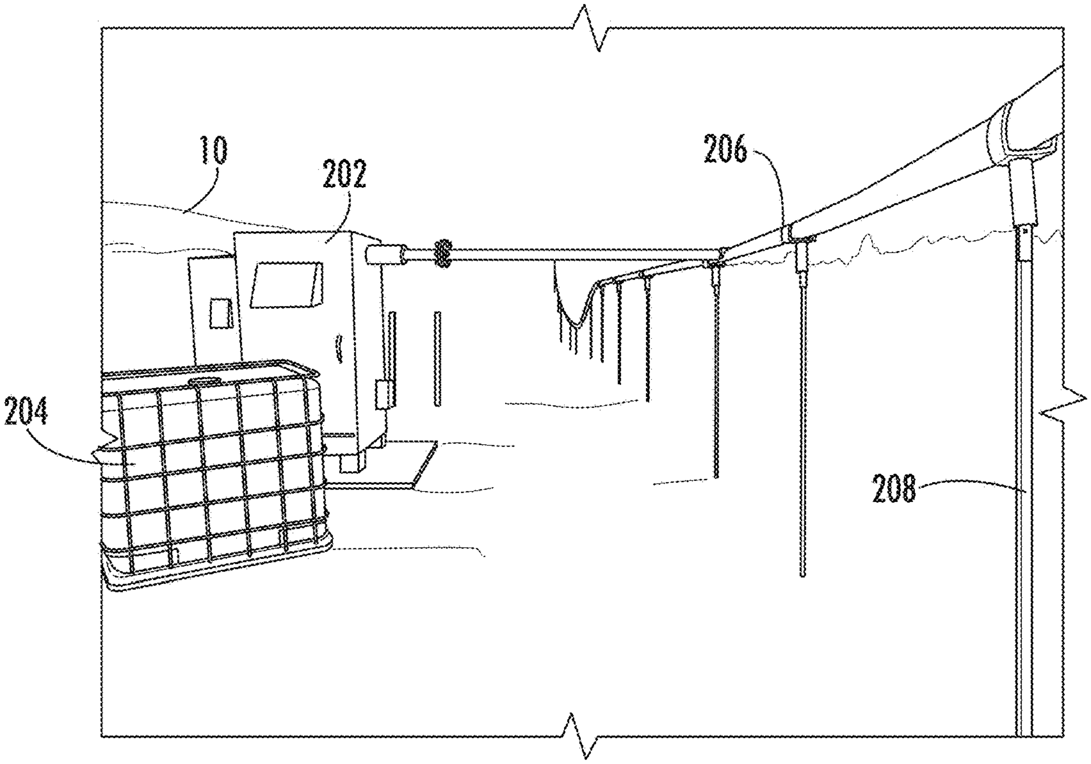
FIG. 8 is a perspective view of a dry vapor device of the system coupled to a plurality of contiguous pipes along a perimeter of a landfill.

In another aspect, the odor control system may use a vaporized nonaqueous chemical as shown in FIGS. 6 and 7. The system does not require a water supply or water pump. Instead, the system relies on a vapor device 202 in fluid communication with a chemical storage tank 204. An air compressor 150 is also carried by the trailer 118 and may be in fluid communication with the at least one nozzle. At least one nozzle 135*b*, for example, is used to disperse the odor neutralizing chemical vapor in the same first direction of the airflow from the discharge opening of the fans 120*a*, 120*b*.

A generator 128 is used to power the equipment carried by the trailer 118 and may be mounted on top of a fuel tank 154 to save space.

Referring now to FIGS. 8-11, a dry vapor device 202 is shown coupled to a chemical storage tank 204 of Phase II of the odor control system. A plurality of contiguous pipes 206 are disposed parallel to a ground surface and along a perimeter of the landfill 10. Each of the pipes 206 have a plurality of nozzles 210 to distribute the odor neutralizing chemicals around the perimeter of the landfill 10. A plurality of vertical support columns 208 carry the pipes 206 above the ground surface. A dry vapor is in fluid communication with the pipes 206 and is dispersed through the plurality of nozzles 210 or apertures. The dry vapor device 202 is in fluid communication with an odor neutralizing chemical supply and generates the dry vapor.

In a particular aspect, the piping 206 comprises 4-inch HDPE pipe perforated with (3/32) inch to (7/32) inch diameter apertures or nozzles. The odor neutralizing chemical vapor is distributed from the piping 206 and suspended in the air similar to the odorous chemicals 110. In addition, the odor neutralizing chemicals are effective yet can be vaporized and stay suspended in the air for extended periods of time.

Figure 9:
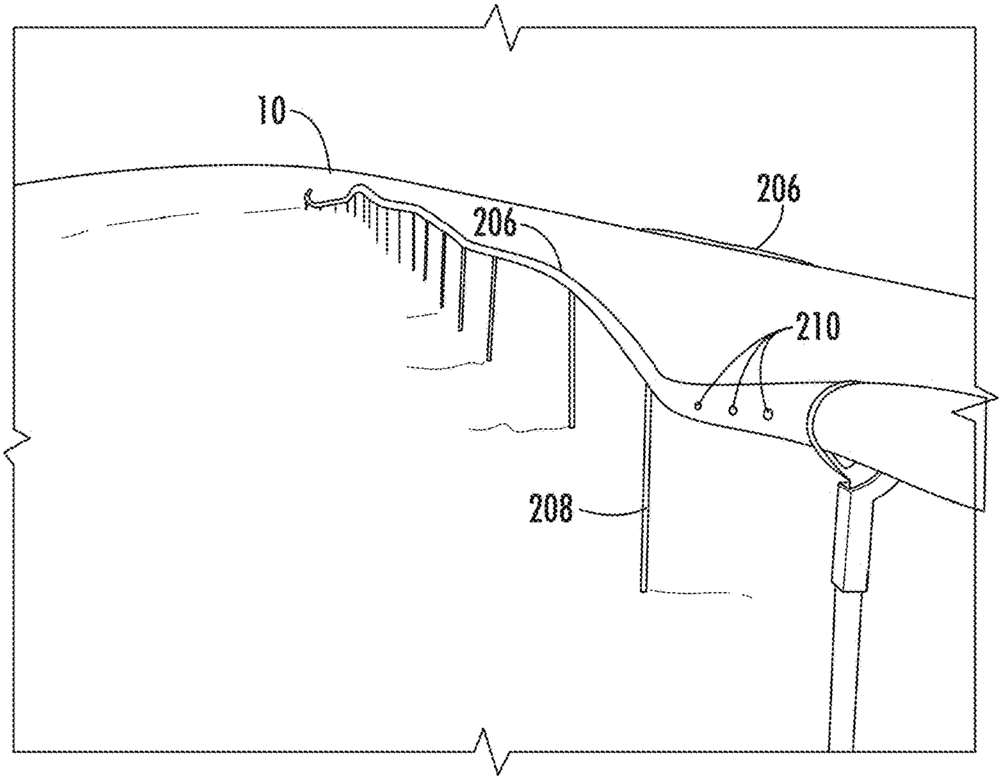
FIG. 9 is a perspective view of the plurality of contiguous pipes installed along a landfill.
Figure 10:
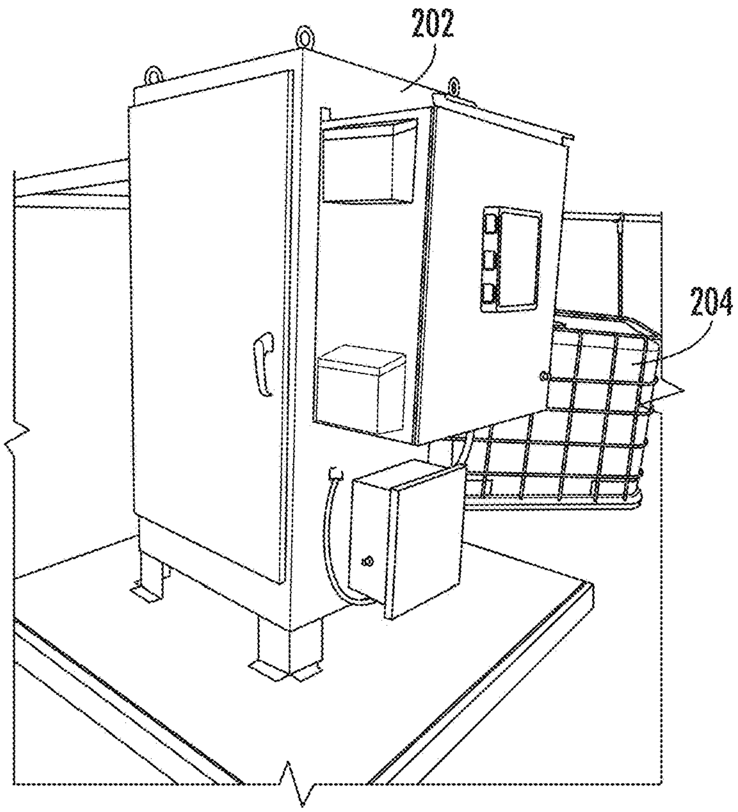
FIG. 10 is a detail view of a housing containing the dry vapor device and fan of FIG. 6.
Figure 11:
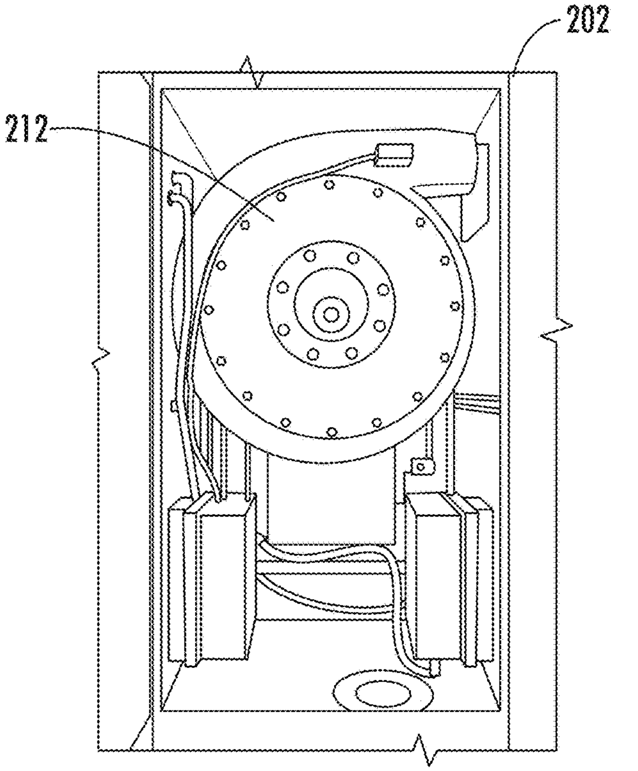
FIG. 11 is a side view inside the housing of FIG. 8 showing the dry vapor device and fan.

As explained above, the piping 206 is supported by vertical support columns 202 or stakes in order to elevate the piping 206 off the ground. A fan or blower 212, shown in FIG. 9 is coupled to the piping 206 in order to distribute the odor neutralizing dry vapor.

The system 100 provides increased spatial coverage over existing systems so that the probability of the odor neutralizing chemicals interacting with the odorous chemicals is increased. In operation, the dry vapor device 202 and associated equipment may require electric power situated preferably at a higher elevation than the piping 206 and require routine operations and maintenance daily checks, and routine chemical replenishment (weekly/biweekly), for example.

Some of the benefits of the dry vapor device 202 include that no water is needed as a carrier, and that the system can be designed site specific using modeling so that it is most effective.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. An odor control system for landfills comprising:
- a dry vapor device configured to generate an odor neutralizing dry vapor without use of water or an aqueous carrier; and
- a plurality of fans configured to be directed at a working face of a landfill, each fan comprising
  - a fan housing having an inlet opening and a discharge opening connected by a passageway therethrough,
  - a blade assembly positioned within the passageway of the fan housing and configured to rotate to generate an airflow from the discharge opening in a first direction,
  - a motor coupled to the blade assembly and configured to drive the blade assembly, and
  - a manifold coupled to a plurality of nozzles in communication with the dry vapor device, the plurality of nozzles being positioned proximate the discharge opening and downstream of the discharge opening, wherein the plurality of nozzles are configured to introduce the odor neutralizing dry vapor into the airflow from the discharge opening in the same first direction;
- wherein the plurality of fans are adjusted to direct the airflow toward the working face and toward adjacent fans such that the airflow from adjacent fans overlaps to form an odor control barrier comprising a suspended volume of odor neutralizing dry vapor around the working face.

2. The odor control system of claim 1, wherein the odor neutralizing dry vapor comprises at least one chemical from an amino hydroxyl group.

3. The odor control system of claim 1, wherein the fan housing comprises a cylindrical shape.

4. The odor control system of claim 1, wherein the blade assembly comprising a plurality of blades extending outward from a central hub.

5. The odor control system of claim 1, wherein the motor is positioned within the passageway of the fan housing.

6. The odor control system of claim 1, further comprising an air compressor in fluid communication with the plurality of nozzles.

7. The odor control system of claim 6, wherein the odor neutralizing dry vapor comprises an odor neutralizing chemical that is entrained into the airflow.

8. The odor control system of claim 1, further comprising:
- a plurality of contiguous pipes in fluid communication with the dry vapor device disposed parallel to a ground surface and along a perimeter of a landfill, each of the pipes comprising a plurality of apertures;
- a plurality of vertical support columns carrying the plurality of pipes above the ground surface; and
- wherein the odor neutralizing dry vapor is configured to be dispersed through the plurality of apertures.

9. An odor control apparatus for landfills comprising:
- a mobile platform configured to be moved to temporary locations proximate a working face of the landfill; and
- an odor control system carried by the mobile platform, the odor control system comprising a dry vapor device configured to generate an odor neutralizing dry vapor without use of water or an aqueous carrier, and a plurality of fans, wherein each fan comprises
- a fan housing having an inlet opening and a discharge opening connected by a passageway therethrough,
- a blade assembly positioned within the passageway of the fan housing and configured to rotate to generate an airflow from the discharge opening in a first direction,
- a motor coupled to the blade assembly and configured to drive the blade assembly, and
- a manifold coupled to a plurality of nozzles in communication with the dry vapor device, the plurality of nozzles being positioned proximate the discharge opening and downstream of the discharge opening, wherein the plurality of nozzles are configured to introduce the odor neutralizing dry vapor into the airflow from the discharge opening in the same first direction;
- wherein the plurality of fans are adjusted to direct the airflow toward the working face and toward adjacent fans such that the airflow from adjacent fans overlaps to form an odor control barrier comprising a suspended volume of odor neutralizing dry vapor around the working face.

10. The odor control apparatus of claim 9, further comprising an odor neutralizing chemical supply carried by the mobile platform and in communication with the dry vapor device.

11. The odor control apparatus of claim 10, further comprising an air compressor in fluid communication with the plurality of nozzles.

* * * * *